United States Patent [19]

Ikenaga et al.

[11] Patent Number: 4,614,410

[45] Date of Patent: Sep. 30, 1986

[54] ULTRASONIC MICROSCOPE WITH OPTICAL MICROSCOPE INCORPORATED THEREIN

[75] Inventors: Katsuzi Ikenaga; Masao Takai; Nobuyuki Nakashima; Koji Umemoto, all of Kudamatsu, Japan

[73] Assignee: Hitachi, Ltd., Tokyo, Japan

[21] Appl. No.: 654,899

[22] Filed: Sep. 27, 1984

[30] Foreign Application Priority Data

Sep. 28, 1983 [JP] Japan ............................. 58-177927

[51] Int. Cl.$^4$ ....................... G02B 21/00; G02B 15/02
[52] U.S. Cl. ..................................... 350/507; 350/520
[58] Field of Search ............................. 350/506–508, 350/511, 520, 522–523, 527, 574; 367/7, 13; 73/601

[56] References Cited

U.S. PATENT DOCUMENTS

| | | | |
|---|---|---|---|
| 3,547,514 | 12/1970 | Hayamizu et al. | 350/520 |
| 4,011,748 | 3/1977 | Bond et al. | 367/7 |
| 4,440,475 | 4/1984 | Colliaux | 350/511 |
| 4,501,476 | 2/1985 | Reinheimer et al. | 350/522 |

FOREIGN PATENT DOCUMENTS

| | | | |
|---|---|---|---|
| 98289 | 10/1924 | Fed. Rep. of Germany | 350/523 |
| 176016 | 10/1982 | Japan | 350/507 |

OTHER PUBLICATIONS

Titan advertisement for Stereo Microscope & Zoom Microscope with Stands, Titan Tool Supply Co., Buffalo, N.Y., 2-1972, Sheet 400-B.

Primary Examiner—William H. Punter
Attorney, Agent, or Firm—Antonelli, Terry & Wands

[57] ABSTRACT

An ultrasonic microscope has an optical microscope disposed in juxtaposition therewith so that the optical microscope can directly observe a specimen to be observed by the ultrasonic microscope, by moving the specimen toward the optical microscope. The optical microscope can also observe a region where an acoustic lens of the ultrasonic microscope and the specimen face each other. For that purpose, the optical microscope is provided with an optical reflector for suiting the view of field of the optical microscope to the region where the acoustic lens and the specimen face each other. Alternatively, the optical microscope is swingably supported so that the view of field of the optical microscope is suited to the region where the acoustic lens and specimen face each other.

6 Claims, 9 Drawing Figures

...

ULTRASONIC MICROSCOPE WITH OPTICAL MICROSCOPE INCORPORATED THEREIN

BACKGROUND OF THE INVENTION

The present invention relates to an ultrasonic microscope, and more particularly to an ultrasonic microscope in which a specimen to be observed by the ultrasonic microscope can be observed by an optical microscope incorporated therein.

In recent years, it has become possible to generate and detect an ultrasonic wave having an ultrahigh frequency as high as 1 GHz and hence to realize an ultrasonic wavelength of about 1.5 μm in the water. As a result, an ultrasonic imaging equipment having a high resolving power has been proposed (see, for example, U.S Pat. No. 4,386,530). FIG. 1 shows the schematic construction of an ultrasonic microscope. Referring to the figure, the transmission, focusing and reception of an ultrasonic acoustic wave is made by an acoustic lens 1 including a cylindrical block of an acoustic propagating medium such as fused quartz one end face of which is polished to provide an optically flat face. On the polished face is disposed a laminated structure which includes upper and lower electrodes 3 with a piezoelectric thin film 2 of zinc oxide or the like sandwiched therebetween. An electric pulse signal 5 from a pulse oscillator 4 is applied to the piezoelectric thin film 2 to generate an ultrasonic acoustic wave 6 therefrom. The other end face of the acoustic lens 1 is provided with a semispherical recess having a diameter of 0.1 to 1.0 mm, and a space between the semispherical recess portion and a specimen 7 is filled with a medium 8 (for example, water) for propagating the ultrasonic wave 6 to the specimen 7. With such a construction, the ultrasonic wave 6 generated from the piezoelectric thin film 2 is propagated through the cylindrical block 1 in the form of a plane wave and is refracted at the semispherical recess portion in accordance with a difference in sound velocity between the fused quartz and the medium 8 so that the plane wave is focused on the specimen 7. The ultrasonic wave reflected from the specimen 7 is collected and converted into a plane wave by the acoustic lens 1. The plane wave is propagated to the piezoelectric thin film 2 to be converted into a radio frequency (RF) signal 9. The RF signal 9 is received by a receiver 10 which includes a diode detector for conversion into a video signal 11. The video signal 11 is used as the input signal of a CRT display unit 12. The specimen 7 is subjected to a two-dimensional scanning in an X-Y plane on the basis of a signal from a power source 13 for driving a specimen table 14. The variation of the intensity of the reflected ultrasonic wave from the specimen 7 thus scanned is two-dimensionally displayed on the screen of the CRT display unit 12.

The acoustic wave used in an ultrasonic microscope has an ultra-high frequency and the attenuation of the acoustic wave in a medium such as water increases in proportion to the second power of the frequency if the transmitting distance is constant. Therefore, it is required to maintain a gap between the acoustic lens 1 and the specimen 7 as small as possible in order to make the transmitting distance short. For example, in the case of an ultrasonic wave having a frequency of 1 GHz, the gap between the acoustic lens 1 and the specimen 7 is selected to be about 50 μm, thereby minimizing the attenuation of the ultrasonic wave. On the other hand, if the semispherical recess portion of the acoustic lens 1 fabricated with high precision is damaged by collision with the specimen, etc. during an observation operation as may take place in an optical lens, the damaged acoustic lens is rendered useless. The above-mentioned requirements of maintaining the gap between the acoustic lens 1 and the specimen 7 very small makes it very difficult to visually ascertain the presence of the gap. The requirements involve a very high possibility that the acoustic lens 1 may be damaged by collision with the specimen 7 during a manipulation of the lens.

SUMMARY OF THE INVENTION

An object of the present invention is to provide an ultrasonic microscope in which a gap between an acoustic lens and a specimen can be readily ascertained, thereby eliminating the above-mentioned inconveniences.

In the present invention, an optical microscope is disposed in juxtaposition with the ultrasonic microscope so that the optical microscope can observe a specimen to be observed by the ultrasonic microscope, by merely moving the specimen into an observable position.

According to one aspect of the present invention, the optical microscope is provided with an optical reflector for allowing the optical microscope to observe a region where an acoustic lens of the ultrasonic microscope and the sample face each other.

According to another aspect of the present invention, the optical microscope is supported so that the optical microscope itself is movable to a position at which it can observe the region where the acoustic lens and the specimen face each other.

BRIEF DESCRIPTION OF THE DRAWINGS

The above and other objects and features of the present invention will be apparent from the following detailed description made referring to the accompanying drawings, in which.

DESCRIPTION OF THE PREFERRED EMBODIMENTS

Now, embodiments of the present invention will be explained below in detail with reference to the accompanying drawings.

Figure 1:
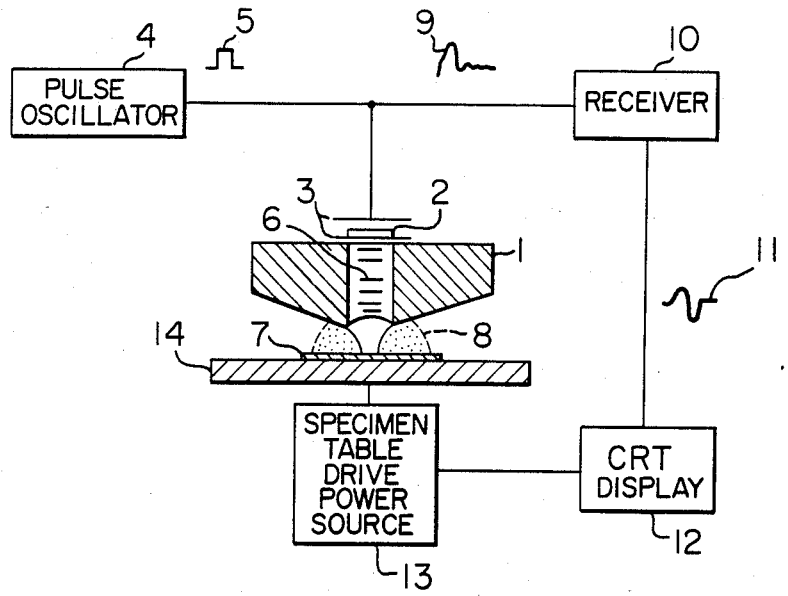
FIG. 1 is a block diagram showing the whole construction of an ultrasonic microscope.
Figure 2:
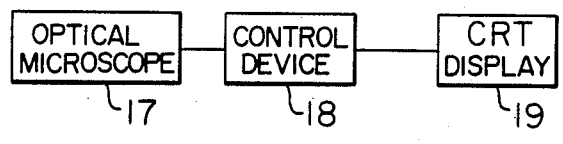
FIG. 2 is a block diagram showing the construction of an optical microscope.
Figure 4:
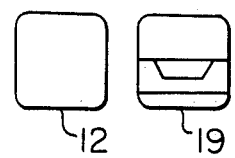
FIG. 4 is front view showing respective display units of an ultrasonic microscope and an optical microscope at the state shown in FIG. 3.

In FIGS. 2 to 5 showing one embodiment of the present invention, the same reference numerals as in FIG. 1 designate like parts or members. Reference numeral 15 designates an acoustic-lens supporting member for supporting and fixing the acoustic lens 1, numeral 16 a base for supporting the specimen table 14 in such a manner that the specimen table 14 for supporting the specimen 7 can move in a two-dimensional plane without making contact with the base 16, and numeral 17 an optical microscope provided in juxtaposition with the acoustic lens 1. The optical microscope 17 is disposed within a moving range of the specimen table 14, and the specimen 7 to be observed by an ultrasonic microscope can be also observed by the optical microscope 17 by merely moving the specimen table 14. As shown in FIG. 2, an image formed by the optical microscope 17 is displayed on a CRT display unit 19 for the optical microscope through a control device 18. The CRT display unit 19 is disposed adjacent to the CRT display unit 12 for the ultrasonic microscope, as shown in FIG. 4. A lens 20 is provided for placing the focus of the optical microscope 17 onto a region where the acoustic lens 1 and specimen 7 face each other. A reflecting mirror 21 disposed on that side of the lens 20 which is remote from the acoustic lens 1, is used for suiting an observable area (namely, field of view) of the optical microscope 17 to the region where the acoustic lens 1 and the specimen 7 face each other so that the optical microscope 17 can monitor the vertical gap therebetween. An optical-system supporting member 22 supports the lens 20 and the reflecting mirror 21 in such a manner that they are spaced apart from each other by a distance determined by the focal length of the lens 20. Also, the optical-system supporting member 22 is disposed so that the focus of the optical microscope 17 is placed onto the region where the acoustic lens 1 and the specimen 7 face each other.

Figure 5:
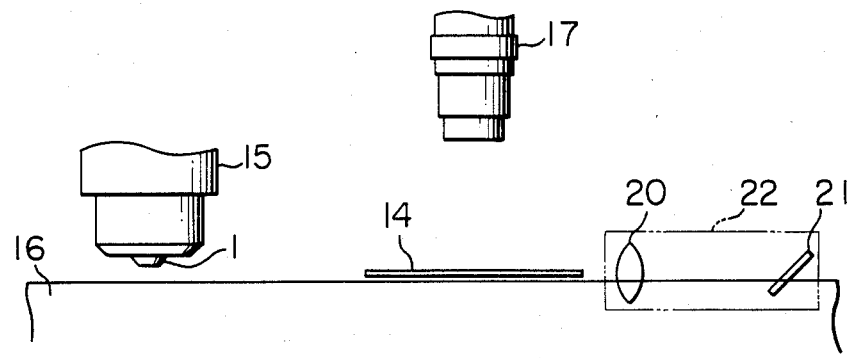
FIG. 5 is a front view of the embodiment shown in FIG. 3 for showing a state that the specimen is observed by the optical microscope.

In the above construction, the specimen 7 on the specimen table 14 is observed by the ultrasonic microscope after the focusing operation of the acoustic lens 1 with respect to the specimen 7 is completed. The focusing operation of the acoustic lens 1 is carried out while observing, the region where the acoustic lens 1 and the specimen 7 face each other, by the optical microscope 17 through the lens 20 and the reflecting mirror 21. More especially, an image formed by the optical microscope 17 is displayed on the CRT display unit 19 to facilitate the ascertainment of a gap between the acoustic lens 1 and the specimen 7. When it is desired to directly observe the specimen 7 by the optical microscope 17, the specimen 7 is placed in the field of view of the optical microscope 17 by moving both the optical-system supporting member 22 and the specimen table 14 as shown in FIG. 5.

With such a construction, the state of the region where the acoustic lens 1 and specimen 7 face each other can be ascertained through the optical microscope 17 by merely providing the optical-system supporting member 22 which is simple in structure. Further, since the observation of the region where the acoustic lens 1 and specimen 7 face each other can be always made during a period when the specimen 7 is observed by the acoustic lens 1 or the ultrasonic microscope, it is possible to prevent the collision of the acoustic lens 1 with the specimen 7.

Though in the present embodiment an image formed by the optical microscope 17 is displayed on the CRT display unit 19 for visual observation, the image formed by the optical microscope 17 may be directly seen by an observer. Further, in the case where a distance between the acoustic lens 1 and the optical microscope 17 is substantially equal to an working distance of the optical microscope 17 defined by a distance between the tip of the optical microscope and an observation point which distance is determined the focal lengths of all lenses involved in the optical microscope inclusive of eye and objective lenses and the arrangement of those lenses, the lens 20 can be omitted.

Figure 3:
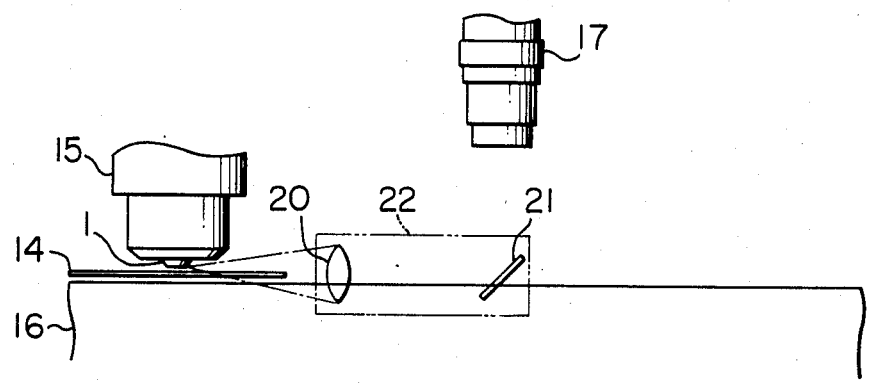
FIG. 3 is a front view of an embodiment of the present invention for showing a state that a region where an acoustic lens and a specimen face each other is observed.
Figure 6:
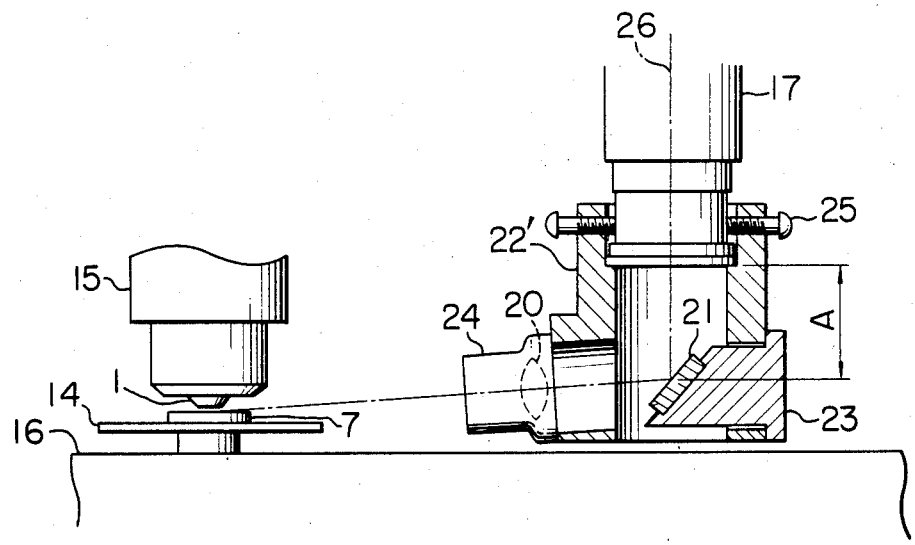
FIGS. 6, 7, 8, and 9 are front views of other embodiments of the present invention, FIG. 8 being a front view of the embodiment shown in FIG. 7 for showing a state that the optical-system supporting member shown in FIG. 7 has been rotated.

Next, another embodiment of the present invention will be explained below with reference to FIG. 6. In FIG. 6, the same reference numerals as in FIGS. 1 to 5 designate like parts or members. The present embodiment has a structure that the optical-system supporting member 22 shown in FIG. 3 is detachably mounted on an end of the optical microscope 17. In FIG. 6, reference numeral 22' designates an optical-system supporting member which is detachably attached to an end of the optical microscope 17 by fixing screws 25. To the optical-system supporting member 22' is attached a reflecting-mirror supporting member 23 which supports the reflecting mirror 21 along the optical axis 26 of the optical microscope 17 at an angle at which the field of view of the optical microscope 17 is suited to the region where the acoustic lens 1 and the specimen 7 face each other. A lens supporting member 24 supports the lens 20 which is disposed between the reflecting mirror 21 and the region where the acoustic lens 1 and specimen 7 face each other. The member 24 is attached to the optical-system supporting member 22', the field of view or observation point of the otpical microscope 17 is at a position away from the tip of the optical microscope 17 by a predetermined working distance A of the optical microscope. Therefore, a focal length of the lens 20 is selected such that an image of the region where the acoustic lens 1 and the specimen 7 face each other can be formed at a position which is away from the optical microscope 17 by the working distance thereof within a space between the optical microscope 17 and the region where the acoustic lens 1 and the specimen 7 face each other.

In the above construction, the observation of the region where the acoustic lens 1 and the specimen 7 face each other is effected by merely mounting the optical-system supporting member 22' on the optical microscope 17. It is apparent that the present embodiment can exhibit the same effects as the embodiment shown in FIG. 3. Of course, the optical microscope 17 is subjected to fine adjustment for the ranging thereof on the specimen 7.

In the present embodiment, when the distance between the acoustic lens 1 and optical microscope 17 is substantially equal to the working distance of the optical microscope 17, the lens 20 may be omitted. Further, an image formed by the optical microscope 17 may be directly seen by an observer without using the CRT display unit 19.

Figure 7:
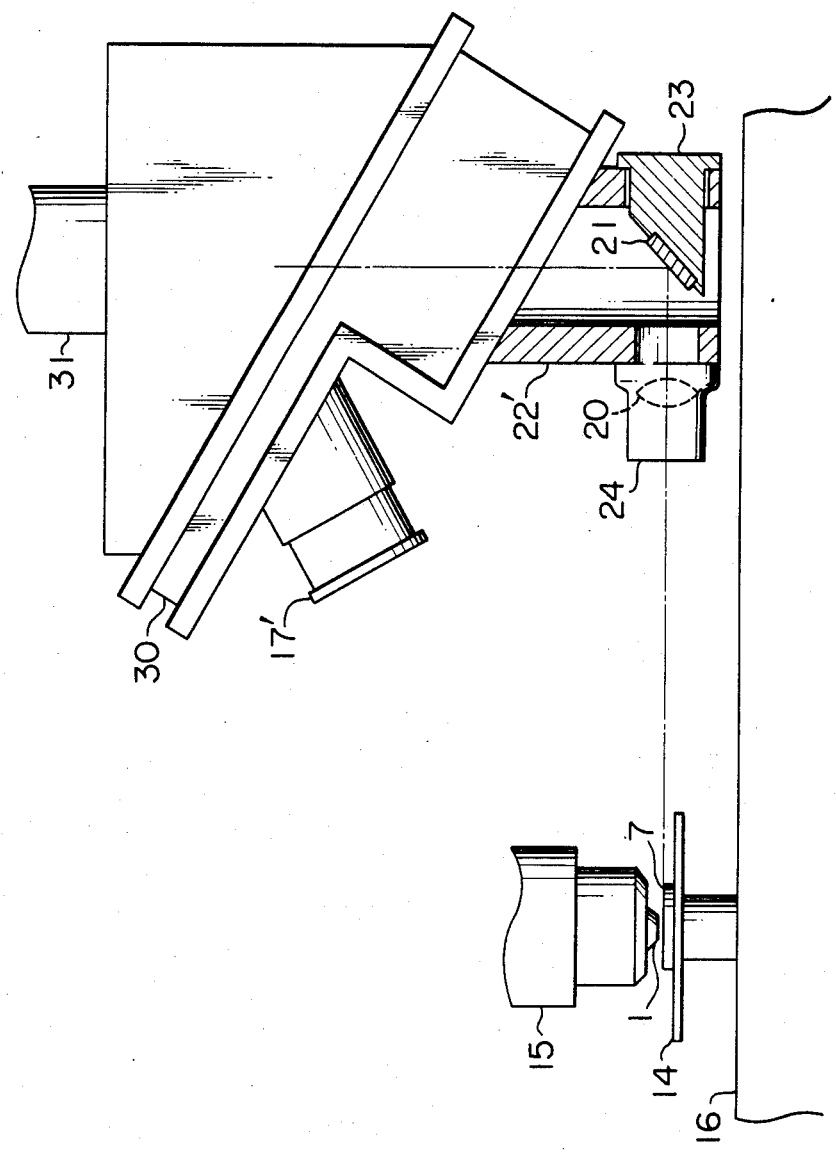
Figure 8:
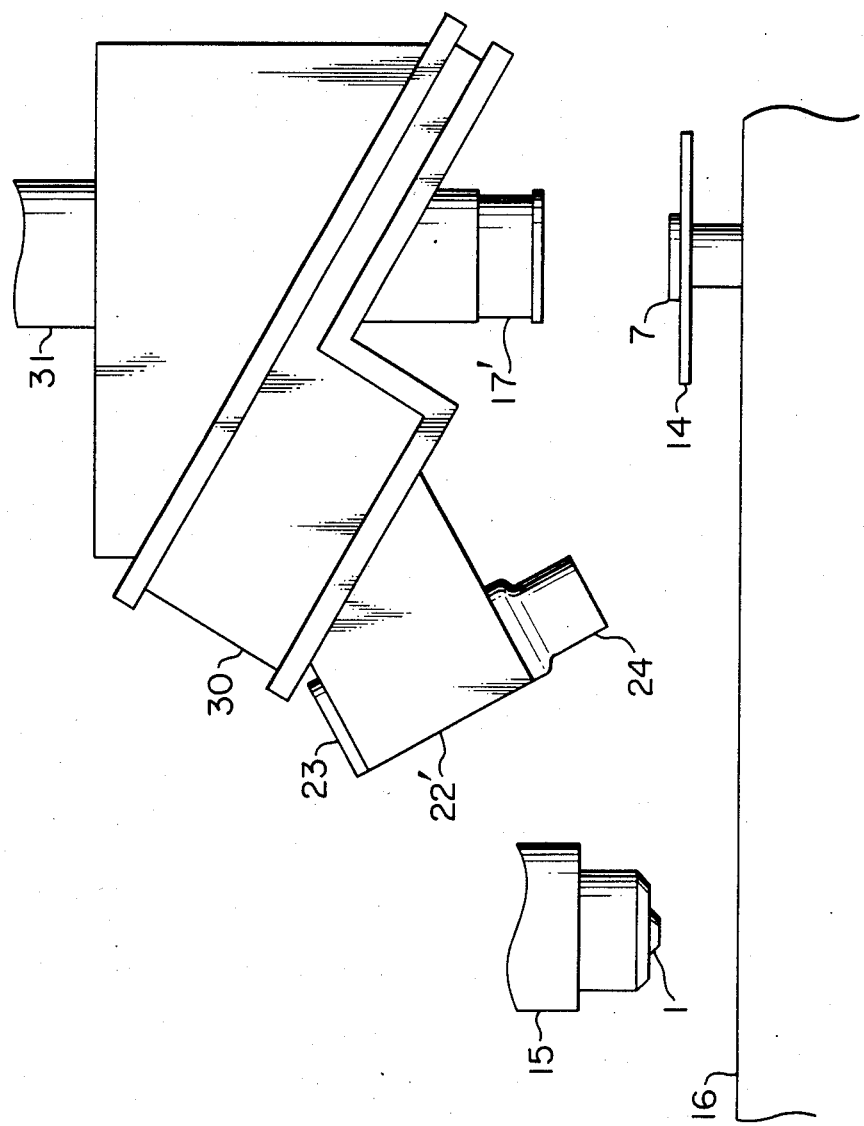

FIGS. 7 and 8 show a further embodiment of the present invention. This embodiment is characterized in that an objective lens 17' of the optical microscope 17 and an optical-system supporting member 22' such as shown in FIG. 6 are mounted on an end of the optical microscope 17 through a rotatable supporting member 30. In order to be able to locate each of the objective lens 17' and the optical-system supporting member 22' on the center axis of the optical microscope 17, the rotatable supporting member 30 is attached with the axis of rotation thereof making member an appropriate angle with the center axis of the optical microscope 17. In the case where the objective lens 17' is located on the center axis of the optical microscope 17, as shown in FIG. 8, the specimen 7 can be directly observed by the optical microscope 17. On the other hand, in the case where the optical-system supporting member 22' is located on the center axis of the optical microscope 17, as shown in FIG. 7, the region where the acoustic lens 1 and the specimen 7 face each other can be observed by the optical microscope 17.

According to such a construction, a mode of the direct observation of the specimen 7 by the optical microscope 17 and a mode of the observation of the region between the acoustic lens 1 and the specimen 7 by the optical microscope 17 can be instantaneously changed over to each other. Accordingly, an operation for observing the specimen can be rapidly performed.

Figure 9:
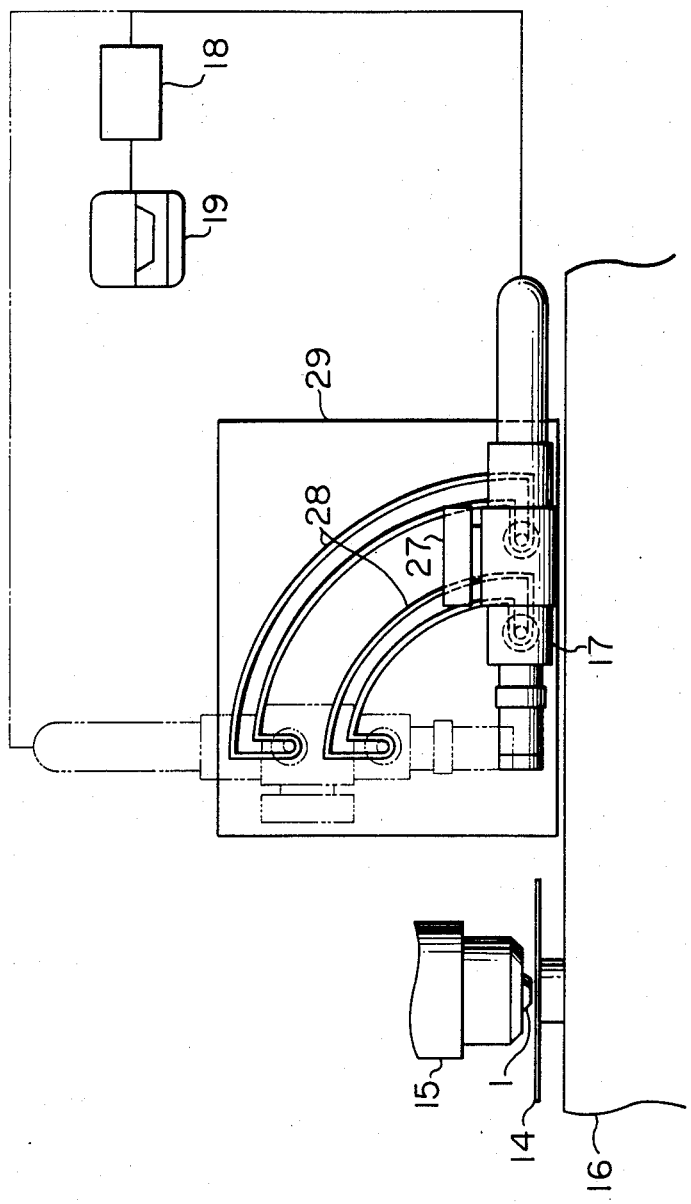

FIG. 9 shows a still further embodiment of the present invention. In this embodiment, the optical microscope 17 itself is swingable for allowing to observe the region where the acoustic lens 1 and the specimen 7 face each other. In FIG. 9, the same reference numerals as in FIGS. 1 to 8 designate like parts or members. Reference numeral 29 designates a supporting member for supporting the optical microscope 17. The supporting member 29 has a guide mechanism 28 for moving the optical microscope 17 to a first position at which the specimen 17 can be directly observed by the optical microscope 17 and to a second position at which the region where the acoustic lens 1 and the specimen 7 face each other can be observed by the optical microscope 17. Reference numeral 27 designates adjusting means for making a distance between the optical microscope 17 and an object to be observed equal to the working distance of the optical microscope 17.

In such a construction, when the specimen 7 is directly observed by the optical microscope 17, the optical microscope 17 is fixed into a vertical position as indicated by dot-dash lines in FIG. 9. On the other hand, in order to observe the region where the acoustic lens 1 and the specimen 7 face each other, the optical microscope 17 is fixed into a horizontal position as indicated by solid lines in FIG. 9. Thus, the optical microscope 17 can be moved into either the vertical or horizontal position.

According to the embodiment of FIG. 9, the suiting of the field of view of the optical microscope 17 to the region where the acoustic lens 1 and the specimen 7 face each other, is effected by moving the optical microscope 17 itself without using additional members as in the previously-mentioned embodiments. That is, it is not required to use the reflecting mirror 21, lens 20 and others, and therefore the number of parts can be reduced. Further, since no additional member is provided on the optical axis of the optical microscope 17, an adjusting operation can be readily performed.

As has been explained in the foregoing, according to the present invention, a gap between an acoustic lens and a specimen can be observed with simple construction, and thus the damage to the acoustic lens can be prevented.

We claim:

1. An ultrasonic microscope comprising:
    ultrasonic wave transmitting and receiving means for transmitting and receiving an ultrasonic wave;
    an acoustic lens for propagating the ultrasonic wave therethrough;
    a display unit for forming and displaying an image based on an ultrasonic wave reflected from a specimen and propagated through said acoustic lens;
    an optical microscope disposed adjacent to said acoustic lens for observing said specimen;
    a specimen table for supporting said specimen thereon and for moving said specimen to a position facing said acoustic lens and a position facing said optical microscope; and
    means for changing the direction of an optical axis of said optical microscope so as to enable said optical microscope to monitor a gap between said acoustic lens and said specimen in a vertical direction in a region where said acoustic lens and said specimen face each other.

2. An ultrasonic microscope according to claim 1, wherein said changing means includes a reflector disposed on the optical axis of said optical microscope for changing the direction of the optical axis of said optical microscope to a direction perpendicular to a direction of propagation of an ultrasonic wave in said acoustic lens.

3. An ultrasonic microscope according to claim 1, wherein said changing means is detachably mounted to an objective lens of said optical microscope.

4. An ultrasonic microscope according to claim 1, wherein said changing means is supported by supporting means for rotatably supporting said changing means and an objective lens of said optical microscope.

5. An ultrasonic microscope according to claim 1, wherein said changing means includes a reflector for changing the direction of the optical axis of said optical microscope through reflection and a lens for adjusting the focus of said optical microscope so as to enable monitoring of said gap between said acoustic lens and said specimen.

6. An ultrasonic microscope according to claim 1, wherein said changing means includes supporting means for rotatably supporting said optical microscope, said supporting means rotating said optical microscope to position the optical axis of said optical microscope to a position for enabling said optical microscope to monitor said gap between said acoustic lens and said specimen.

* * * * *